US007775969B2

(12) United States Patent
Teichmann

(10) Patent No.: US 7,775,969 B2
(45) Date of Patent: Aug. 17, 2010

(54) ENDOSCOPE WITH AN OPTICAL FIBER EMBEDDED IN A FLEXIBLE SLEEVE AND METHOD FOR USING THE SAME

(75) Inventor: Heinrich-Otto Teichmann, Katlenburg-Lindau (DE)

(73) Assignee: LISA Laser Products OHG Fuhrberg & Teichmann, Katlenburg-Lindau (DE)

( * ) Notice: Subject to any disclaimer, the term of this patent is extended or adjusted under 35 U.S.C. 154(b) by 497 days.

(21) Appl. No.: 11/401,037

(22) Filed: Apr. 10, 2006

(65) Prior Publication Data

US 2006/0235270 A1    Oct. 19, 2006

(30) Foreign Application Priority Data

Apr. 14, 2005 (DE) .................. 10 2005 017 204

(51) Int. Cl.
*A61B 1/00* (2006.01)
*A61B 1/12* (2006.01)
*A61B 1/04* (2006.01)

(52) U.S. Cl. ............... 600/106; 600/155; 600/153; 600/156; 600/121

(58) Field of Classification Search .......... 600/106, 600/121–125, 153, 155, 156
See application file for complete search history.

(56) References Cited

U.S. PATENT DOCUMENTS

| 2,571,653 | A | | 10/1951 | Bastien ............... 128/218 |
| 3,809,072 | A | | 5/1974 | Ersek et al. ............... 128/23 |
| 4,741,326 | A | * | 5/1988 | Sidall et al. ............. 600/123 |
| 4,798,193 | A | * | 1/1989 | Giesy et al. ............. 600/114 |
| 4,886,049 | A | * | 12/1989 | Darras ................... 600/124 |
| 4,920,961 | A | * | 5/1990 | Grossi et al. .............. 606/14 |
| 4,979,496 | A | * | 12/1990 | Komi ..................... 600/113 |
| 5,415,157 | A | * | 5/1995 | Welcome ................. 600/121 |
| 5,549,601 | A | * | 8/1996 | McIntyre et al. ........... 606/15 |
| 5,573,493 | A | * | 11/1996 | Sauer et al. ............. 600/121 |
| 5,575,756 | A | * | 11/1996 | Karasawa et al. ........ 600/157 |
| 5,704,899 | A | * | 1/1998 | Milo ..................... 600/161 |
| 5,746,694 | A | * | 5/1998 | Wilk et al. .............. 600/123 |
| 5,817,061 | A | * | 10/1998 | Goodwin et al. ....... 604/164.03 |
| 5,820,546 | A | * | 10/1998 | Ouchi ................... 600/123 |
| 5,827,177 | A | * | 10/1998 | Oneda et al. ............ 600/121 |
| 5,836,287 | A | * | 11/1998 | Yano et al. .............. 123/478 |
| 5,879,287 | A | * | 3/1999 | Yoshihashi .............. 600/160 |
| 5,938,587 | A | * | 8/1999 | Taylor et al. ............ 600/139 |
| 6,224,566 | B1 | * | 5/2001 | Loeb ..................... 604/22 |
| 6,908,428 | B2 | * | 6/2005 | Aizenfeld et al. ......... 600/123 |
| 7,341,555 | B2 | * | 3/2008 | Ootawara et al. ......... 600/106 |
| 2003/0073955 | A1 | * | 4/2003 | Otawara ............... 604/164.01 |
| 2003/0236517 | A1 | | 12/2003 | Appling ................... 606/7 |
| 2004/0010248 | A1 | * | 1/2004 | Appling et al. ............ 606/15 |

* cited by examiner

*Primary Examiner*—Linda C Dvorak
*Assistant Examiner*—Alireza Nia
(74) *Attorney, Agent, or Firm*—Thomas, Kayden, Horstemeyer & Risley, LLP

(57) ABSTRACT

The present invention relates to an endoscope, in particular an ureterorenoscope. The endoscope comprises a lumen for insertion of a light and energy transmitting fiber. According to the invention during insertion of the fiber into a working channel of the endoscope the sharp edges of the fiber are protected by a flexible sleeve in order to avoid damages of a wall limiting the working channel. Prior to using the fiber for transmitting energy emitted by a laser the flexible sleeve is completely removed from the working channel in order to free a lumen that might be used for additional instruments or delivery of a fluid. Furthermore the stiffness of the endoscope is reduced by removing the flexible sleeve.

6 Claims, 2 Drawing Sheets

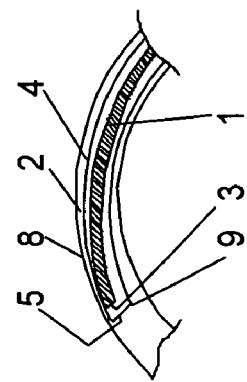
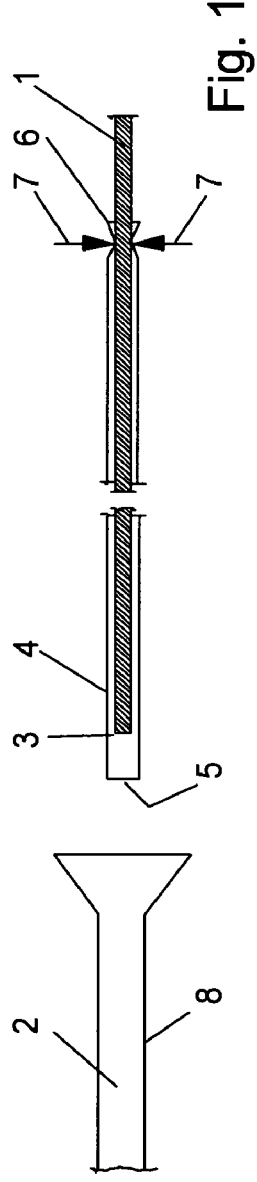
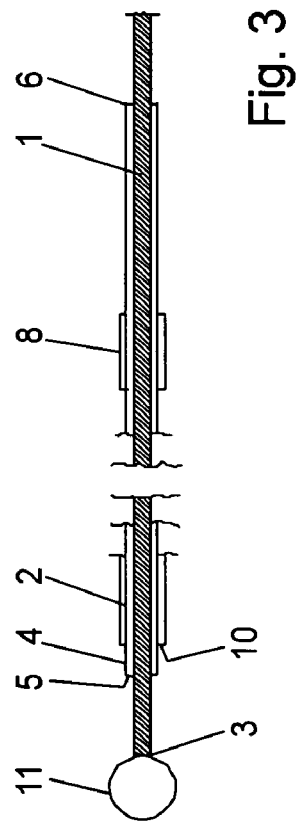
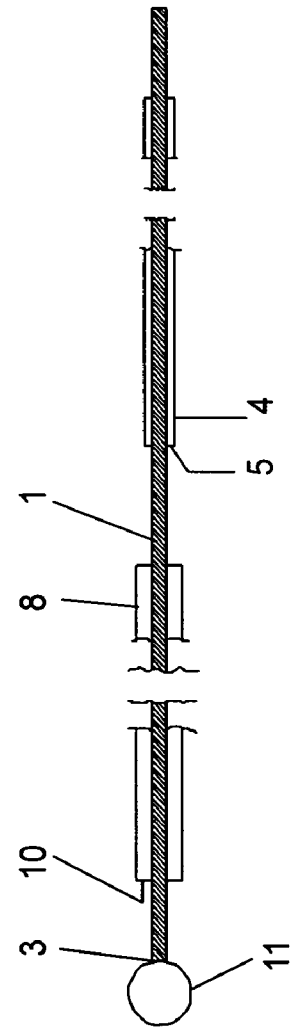

ENDOSCOPE WITH AN OPTICAL FIBER EMBEDDED IN A FLEXIBLE SLEEVE AND METHOD FOR USING THE SAME

CROSS REFERENCE TO RELATED APPLICATIONS

This application claims priority to co-pending German Patent Application No. DE 10 2005 017 204.0 entitled "Schutzvorrichtung und Verfahren für das Einführen eines langgestreckten Instruments in einen Arbeitskanal", filed Apr. 14, 2005.

FIELD OF THE INVENTION

The present invention generally relates to an endoscope for multiple use for medical purposes in a body of a mammal. Furthermore, the present invention relates to a method for using such endoscope. More particularly, the present invention relates to an endoscope with an optical fiber located in a working channel of the endoscope wherein an inner wall limiting the working channel is protected against damages caused by a distal end of the optical fiber. The endoscope might be an ureterorenoscope. Besides the aforementioned use of the endoscope the endoscope might also be used in other technical fields and appliances besides medicine.

BACKGROUND OF THE INVENTION

When using flexible endoscopes in medical endoscopy one or a plurality of working channel(s) is limited by a tube or sheet made of plastic. One such channel is used for visually inspecting a target area and/or the path the endoscope takes inside a body. Other working channels might be used for delivering a transparent fluid for rinsing the target area of the endoscope, in particular the target area of a minimal invasive surgical operation. Furthermore, it is possible to use the working channels for introducing additional instruments, in particular instruments used for surgery. Such instruments include micropliers, guiding wires, small baskets for recovery of particles or material from the target area, e.g. smashed or wrecked urinary stones, as well as light transmitting fibers, in particular fibers transmitting the light emitted by a laser. It is one drawback of the known endoscopes that the flexibility of an endoscope might be reduced in an operational state by an instrument extending at least partially through the working channel. In order to avoid problems caused by such reduced flexibility the endoscopes are commonly introduced in a body without an instrument extending through the working channel. Subsequent to introducing the empty endoscope into the body the instruments are introduced into the working channel. Also from other reasons it might be necessary to introduce instruments into the working channels of an endoscope after inserting the endoscope inside a body. On example is a visual investigation of the lower calyces renales by a flexible ureterorenoscope in order to locate nephroliths and for subsequent fragmentation of the nephroliths and/or removal of the nephroliths. In such procedure it is helpful for the purpose of detecting the nephroliths to maintain an unlimited flexibility of the flexible ureterorenoscope using the whole lumen of the working channel for rinsing the optical target area. This means that an instrument used for subsequent fragmentation or retrieval of the nephroliths should not be introduced into the working channel of the ureteror-endoscope when trying to detect the nephroliths. It is preferred to use energy supplied by a laser and transmitted or delivered by a fiber for the fragmentation of nephroliths or urinary calculus. Such fiber usually comprises a distal end cut perpendicular to its optical axis in order to provide optimal contact of the blunt distal end with the urinary calculus that is to be fragmented. In spite of the used fibers being designed to reduce the flexibility of the endoscope as little as possible, introduction of the fibers into the working channel of a flexible endoscope still involves problems. Due to a remaining small stiffness of the fiber, in particular a glass fiber, a sharp end of the distal end of the fiber scratches or cuts the wall that limits the working channel. Such undesired effect causes damages of the surface of the inner wall of the endoscope or the fiber. The damages in particular occur in curved portions of the working channel. For a long term use, such effect might cause failure of the endoscope. In practice, up to every second maintenance work for flexible endoscopes is due to damages of the working channel caused by an introduction of an instrument or a fiber into the working channel. Each of such maintenance works might cause costs of more than US $1,000.

Whereas the present invention relates to endoscopes for multiple use with at least one lumen used for transmitting an optical signal to the physician, US 2003/0236517 A1 relates to a medical device for treatment of blood vessels using an introducer catheter for applying endovascular laser therapy. Usually, such introducer catheters are designed for single use due to the low costs of such catheter involving less costs for using a new catheter for the next body to be treated than disinfecting a used catheter. Such single use catheter comprises a protective sleeve with a single lumen with the optical fiber positioned therein. When moving the fiber through the working channel of the catheter, the distal end of the fiber is located inside the flexible sleeve such that a distal end of the flexible sleeve covers the edges built by the distal end of the fiber. In such manner, any damages of the limiting wall of the working channel are avoided. For a treatment of a saphenous vein, a small gauge needle is used to puncture the skin and access the vein. A guide wire is advanced into the vein through the lumen of the needle. The needle is then removed leaving the guide wire in place. A hemostasis introducer sheet is introduced into the vein over the guide wire and advance to 1 to 2 cm below the sapheno-femoral junction. A valve gasket provides a leak-proof seal to prevent a backflow of blood out of the sheet's proximal opening while simultaneously allowing the introduction of the fiber into the sheet. The valve gasket is made of elastomeric material such as rubber or latex. The gasket opens to allow insertion of the optical fiber and then seals around the protective sleeve containing the optical fiber. When inserting the optical fiber into the vein, the distal end of the fiber is protected by the protective sleeve. The distal end of the fiber embedded in the protective sleeve is inserted into the hemostasis sheet and advanced forward through the sheet lumen. As the protected fiber assembly is advanced through the curved pathway of the sheet shaft, the non-traumatic sleeve tip rather than the sharp edge of the optical fiber comes in contact with the inner sheet wall. Advantageously, the sleeve tip does not damage the inner wall of sheet shaft as it is advanced because of the sleeve's flexible material characteristics as well as because of its tapered or radiuses, non-traumatic distal profile. Moreover, the device eliminates the shavings of material of the working channel that may be cut away from the inner wall of the sheet shaft as an unprotected fiber tip is advanced. Accordingly, there is no risk of shaft material being deposited within the venous system or becoming adhered to the flat face of the optical fiber when the protective fiber assembly is used for transmitting laser energy. The fiber and the protective sleeve are advanced through the working channel until a connecting element comes in contact with a handle of the catheter. Once fully assembled the handle restricts relative movement of the protective sleeve with respect to the fiber as well as the working channel to a small range. Such range comprises a first limiting position correlating with an operational state wherein the distal end of the optical fiber is located inside the flexible sleeve. A second limiting position correlates with another operational state wherein the distal end of the optical fiber protrudes from the distal end of the protective sleeve. Once the physician has confirmed that the tip of the optical fiber is correctly positioned approximately 1 to 2 cm below the saphenous-femoral junction the device is placed in an operating position with the distal end of the fiber located outside the sleeve. The distal end of the fiber is exposed by retracting the connecting distal handle component while holding the proximal handle component stationary. The device is then in operating position, ready to delivery of laser energy to the diseased vein. After such treatment of the target area by the energy of a laser the catheter is then slowly withdrawn through the vein, preferably at a rate of 1-3 mm per second.

Further prior art is known from U.S. Pat. No. 2,571,653, U.S. Pat. No. 3,809,072 and U.S. Pat. No. 4,886,049.

SUMMARY OF THE INVENTION

In the past, the conflict between mobility of flexible ureterorenoscopes and laser fibers required a two-step procedure: For diagnosis, localization and identification of stones in the lower calices the unrestricted mobility of the instrument's flexibility has to be available. Accordingly such steps were performed with an "empty" working channel having a large flexibility. For fragmentation of urinary stones a minimum of 15-20 Watt of laser power is required. Unfortunately, in the physics of some lasers there is limit in reducing the fiber diameter. Also very thin laser fibers are delicate and may break in use or even before they are used. Hence for stone therapy laser fibers with an optical core of 20 to 30 μm are common. However, even fibers at this diameter reduce the mobility of the ureterorenoscope due to their stiffness and friction in the working channel. Following the decision for laser fragmentation the flexible ureterorenoscope needed to be straightened again and the laser fiber was forwarded. Forwarding a laser fiber into a deflected or curved ureterorenoscope may immediately cause damage to the working channel because of the sharp silica glass at the distal end of the fiber. Therefore the surgeon will straighten the ureterorenoscope again after the stone has been located in order to insert the laser fiber without damaging the working channel. Subsequently, a second search for the stone with the laser fiber protruding out of the instrument is undertaken. During the second search the mobility of the ureterorenoscope is restricted because of the fiber being inside the working channel. Also the fiber needs to protrude out of the ureterorenoscope and while manipulating the instrument the tip of the fiber may cause trauma and bleeding which impairs the endoscopic view. As a result, the required time for the second search for the stone is about the same as for the first search which extends the operational time considerably.

The present invention has identified a simple requirement: it needs to be feasible to insert a laser fiber for stone therapy into any deflected ureterorenoscope without causing damage to the working channel and without having an impact on the deflection of the ureterorenoscope in order to maintain the visual contact to the stone.

On the basis of the invention the aforementioned straightening in a second step is not necessary any more. According to the invention, still outside of the ureterorenoscope the laser fiber is inserted into the flexible sleeve until the tip of the fiber stands approximately 2 to 5 mm behind the distal tip of the flexible sleeve. In this position, a Touhy Borst adapter at the proximal end of the flexible sleeve might be locked to the fiber. The combination of the flexible sleeve and the laser fiber is inserted into the deflected ureterorenoscope and forwarded until it appears in the endoscopic view. During insertion into the ureterorenoscope the flexible sleeve is leading with respect to the laser fiber by a few millimeters. Therefore, any contact of the laser fiber to the working channel and damage is prevented. Due to appropriate selection of the materials for the flexible sleeve there might be avoided any noticeable friction. Finally, the Touhy Borst adapter is opened and the laser fiber is forwarded the last few millimeters towards the stone.

The use of the flexible sleeve might cause savings of approximately 70% of the repair works for damaged ureterorenoscopes. On the other hand, the use of the flexible sleeve is saving theater time because the second search for the stone is not required any more. Furthermore, the use of the flexible sleeve might also encourage the use of holmium lasers for the therapy of lower calyx stones in conjunction with flexible ureterorenoscopes and to reduce the surgeons fear of destroying a valuable instrument.

According to the invention the relevant device is an endoscope for multiple use. Such endoscope comprises a working channel, an optical fiber having a distal end and a flexible sleeve. The flexible sleeve has an inner lumen for receiving said optical fiber. The flexible sleeve is axially movable relative to the working channel and relative to the optical fiber. The endoscope is designed and arranged for allowing a reciprocating movement, in particular a repeated movement in forward and backward direction throughout one procedure of treating a human body. The movement results in a first operational state of the endoscope wherein the distal end of the optical fiber is located inside the flexible sleeve. Quite similar to US 2003/0236517 A1 the first operational state corresponds to a protected state which allows an introduction and a withdrawal of the optical fiber embedded into the flexible sleeve into the working channel. Furthermore, the movement results into a second operational state wherein the flexible sleeve is completely removed from said working channel. This means that differing from US 2003/0236517 A1, it is possible to free a lumen built between the wall limiting a working channel and the outer circumference of the optical fiber from the protective sleeve. This is possible with the endoscope located inside the body. Such freed lumen might be used for introducing additional instruments into the endoscope for manipulating a target area of the endoscope. However, it is also possible to use such lumen for introducing a fluid for rinsing the target area of the endoscope or the optical fiber. Whereas according to US 2003/0236517 A1 such lumen is blocked by the protective sleeve causing the need for additional lumen in case of a fluid being delivered to the target area, the embodiment of the invention might lead to a very smart design of the endoscope with small outer diameters of the endoscope. Furthermore, fluid might be supplied with large volumetric flows wherein the fluid exits the endoscope close to the optical fiber and the target area. Additionally, it has been observed that the flexible sleeve located inside the endoscope might change the mechanical properties of the endoscope by enforcing the endoscope and increasing the stiffness of the endoscope. Such stiffening effects can be avoided by removing the flexible sleeve when transferring the endoscope in the second operational state. Nevertheless, it is also possible to provide an endoscope according to the present invention with additional lumens.

The optical system for inspecting the target area of the endoscope and for finding a desired path in the body might be located in the same lumen as the optical fiber or might be located in an additional or main lumen.

Accordingly for one embodiment of the invention the endoscope comprises a first lumen containing an optical system for guiding the endoscope and/or inspecting a target area inside the body and an additional second lumen for inserting a fiber with the protective sleeve and transmitting light from a laser source via the fiber.

According to another embodiment of the invention, the endoscope comprises a third operational state. In such third operational state, the flexible sleeve extends through said working channel but said distal end is located outside said sleeve. Such third operational state more or less correlates with the operating position according to US 2003/0235617 A1. Such third operational state provides an endoscope with increased stiffness due to the small stiffness of the sleeve. However, the whole flexible sleeve might also be completely removed from the working channel when transferring the endoscope into the second operational state. According to such embodiment, a multifunctional use of the endoscope is possible providing the possibilities of adapting the endoscope to different types of use and conditions inside the body of a human being.

For completely removing the flexible sleeve from the working channel, another embodiment of the invention suggests to use a slotted flexible sleeve. When retracting the sleeve from the endoscope, the sleeve might be separated from the optical fiber in the exit region of the flexible sleeve from the working channel by passing the fiber through the slot. For reintroducing the flexible sleeve into the working channel, the distal end of the slot is passed over the optical fiber and then subsequently introduced into the working channel.

According to an alternative embodiment of the invention, the length of the optical fiber is longer than the double of the length of the maximum of the length of the sleeve and the length of the working channel. This means that the flexible sleeve might be completely withdrawn from the endoscope while still housing the optical fiber. Throughout further medical procedures, the flexible sleeve is left in such position containing the optical fiber. After finishing the medical procedure, the flexible sleeve is moved in distal direction reintroducing the flexible sleeve into the working channel.

According to another embodiment of the invention, the flexible sleeve is made of PTFE. Such material is very robust and durable. Furthermore, PTFE comprises a very low friction coefficient. Additionally, the static friction coefficient of PTFE might equal the dynamic friction coefficient such that stick-slip-movements might be avoided by use of such material. PTFE is also a robust material when used in combination with acid or alkaline materials.

In another aspect of the invention, the flexible sleeve has a slanted distal tip. Such slanted distal tip has the effect that curvatures of the working channel being directed in the same direction as the slanted tip might be followed by the whole abutting face of the distal end resulting in smaller surface pressure at the limiting wall of the working channel. This leads to a reduction of damages of the limiting wall. However, also in cases of the curvature of the working channel being directed in opposite direction to the slanted distal tip, the edge of the distal tip contacting the limiting wall of the working channel is not supported by the whole cross-section of the flexible sleeve but the remaining reduced cross-section of the slanted distal tip. This means that the forces necessary to deflect the distal tip for an adaptation to the curvature are reduced compared to an unslanted distal tip which again leads to a reduction of damages of the limiting wall of the working channel.

For a method for using an endoscope according to the invention, in a first step the optical fiber is embedded in the flexible sleeve in a first operational state wherein the distal end of the optical fiber is located inside the flexible sleeve. Then, the flexible sleeve with the optical fiber embedded therein is introduced into a working channel of the endoscope. The flexible sleeve is moved relative to the optical fiber and relative to the working channel until a second operational state is reached. In such second operational state the whole flexible sleeve is located outside the working channel. Access is given to a lumen by removing the flexible sleeve from the interior of the working channel. Such lumen is limited by a wall limiting the working channel and limited by the outer circumference of the fiber. Such lumen is then used or for a diagnostic purpose or for a therapeutic purpose, e.g. for introducing an instrument into said lumen or for using the lumen for delivery or collection of a fluid. Afterwards, the flexible sleeve is reintroduced into the working channel. Then, the flexible sleeve with the fiber located therein is removed from the endoscope. Here, it is possible first to remove the endoscope from the body and afterwards removing the flexible sleeve from the endoscope. However, it is also possible first to remove the flexible sleeve from the endoscope and then to remove the endoscope with decreased stiffness from the body.

One component of the endoscope according to the invention is a flexible sleeve embedding or covering the distal end of the fiber such that during introduction of the fiber into the working channel, the distal end of the protective sleeve protrudes from the distal end of the fiber. Accordingly, the distal end of the fiber does not directly contact the wall limiting the working channel when introducing the fiber into the working channel. However, the flexible sleeve covers any sharp edges of the distal end of the fiber. Additionally, the protective sleeve protrudes from the distal end of the fiber. Accordingly, the distal end of the flexible sleeve approaches any curved regions of the working channel prior to the distal end of the fiber approaching these regions. Accordingly, the flexible sleeve adapts to any curvatures of the working channel before the distal end of the fiber inside the flexible sleeve approaches these curvatures. With other words, the wall limiting the working channel only leads the flexible sleeve when introducing the fiber in the curved regions of the working channel instead of guiding the sharp distal end of the fiber. Furthermore, the proximal end region of the flexible sleeve protrudes from the working channel providing access for the physician to the sleeve for manipulating the position of the sleeve with respect to the fiber as well as the working channel. For the fiber located in the target area, such manipulation allows pulling back the flexible sleeve such that the distal end of the fiber is located outside the sleeve. In such operational state, energy might be activated and delivered by the fiber to a target area.

The proximal end of the flexible sleeve might be equipped with a fixing device. Such fixing device is used for temporarily fixing the relative position of the fiber inside the flexible sleeve. Such fixation might be used when introducing the unit of flexible sleeve and fiber into the working channel. Furthermore, it is possible to fix the distance of the distal end of the fiber protruding from the flexible sleeve in the third operational state. It is preferred to choose a material for the protective sleeve with a sufficient sheer strength. The distance the sheet protrudes from the distal end of the fiber in the first operational state might be some millimeters, e.g. in the range of 1 to 5 mm.

The outer diameter of the flexible sleeve should be smaller than the inner diameter of the working channel. Furthermore, the inner diameter of the protective sleeve should be chosen to be larger than the outer diameter of the fiber. Such dimensions reduce friction between the working channel and the flexible sleeve as well as between the flexible sleeve and the fiber. Additionally, the friction depends on the material of the flexible sleeve. Here, a material with a low friction coefficient should be chosen. Furthermore, a material with a large flexibility with respect to a lateral deflection of the flexible sleeve should be chosen. Additionally, the flexibility might be influenced by the dimension of the wall thickness of the flexible sleeve which might be chosen in the range of approximately $0.5^{th}$ to $2^{th}$ of a millimeter, in particular $1^{th}$ of a millimeter.

The flexible sheet might be chosen to be a tube. The fiber might be a fiber for transmitting light with a blunt end region. In particular, the fiber could be a cut glass fiber with a sharp leading edge.

The working channel for housing both the fiber and the flexible sheet is preferably part of a flexible endoscope and might be built by a tube made of a flexible plastic material.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 1 shows the proximal end region of a fiber and a flexible sleeve surrounding the fiber prior to introduction into a working channel.

FIG. 2 shows a distal end region of the fiber and the flexible sleeve according to FIG. 1 during introduction and advancement in a working channel in a curved region of the working channel.

FIG. 3 shows the distal and proximal end regions of the working channel, wherein the fiber protrudes with its distal end from the distal end region of the working channel, the distal end region of the fiber being located adjacent to an urinary stone wherein the flexible sleeve is retracted to free the distal end region of the fiber.

FIG. 4 shows a configuration similar to that of FIG. 3, wherein the flexible sleeve is completely pulled back in proximal direction and removed from the working channel.

DETAILED DESCRIPTION

Figure 5:
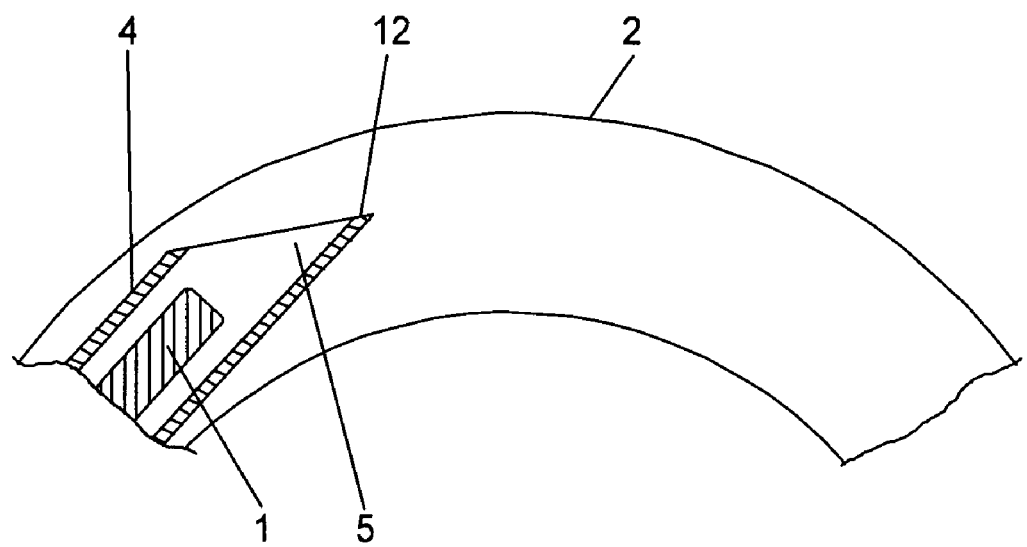
FIG. 5 shows a slanted distal end region of a flexible sleeve with a fiber located therein during advancement of the flexible sleeve and the fiber through a curved region of the working channel.

Referring now in greater detail to the drawings, FIG. 1 illustrates an oblong instrument 1 which in the present case might be a fiber or glass fiber for transmitting light emitted by a laser. The oblong instrument 1 is designed and arranged to be introduced into a working channel 2. The working channel 2 in particular is built by a flexible endoscope, e.g. a ureter-orenoscope. Such working channel 2 is arranged parallel to an optical main channel of the endoscope. In order to provide the possibility to introduce instrument 1 into the working channel 2, the distal end region 3 of instrument 1 is covered, jacketed or housed in the flexible sleeve 4 or flexible tube, wherein the distal end region of the flexible sleeve 4 protrudes from the distal end region 3 of instrument 1. The proximal end region 6 of the flexible sleeve 4 is fixed at instrument 1 or pressed against instrument 1 which is indicated by arrows in FIG. 1. In case of the flexible sleeve 4 having a sufficient sheer stiffness or longitudinal stiffness, the fixation of the flexible sleeve at its proximal end region 6 guarantees that the distance the distal end region 5 protrudes from the distal end region 3 of instrument 1 does not vary.

FIG. 2 shows the flexible sleeve 4 when introducing the flexible sleeve 4 with an instrument 1 located therein into a curved region of the working channel 2. In such curved region, there is the danger of "shaving", cutting or abrading the limiting wall 8 of the working channel 2 by edges of the distal end region 3 of instrument 1 which might cause damages of working channel 2. The flexible sleeve 4 provides a lateral cover for the distal end region 3 of instrument 1. Additionally the distal end region 3 is guided by the protruding distal end region 5 of flexible sleeve through the curved region of the working channel. The limiting wall 8 of working channel 2 deflects the flexible protruding distal end region 5 of flexible sleeve 4 when advancing instrument 1 by pushing the flexible sleeve 4. The flexibility of the distal end region 5 of flexible sleeve 4 which is larger than the flexibility of the fiber or instrument 1 avoids damages of the wall 8. Furthermore, damages are avoided due to the fact that the outer diameter of the flexible sleeve 4 better approximates the inner diameter of working channel 2 than the outer diameter of instrument 1. Additionally, the material of the flexible sleeve 4 might be chosen such that the friction coefficient between the flexible sleeve 4 and the limiting wall 8 is decreased. On the other hand damages of the wall 8 might be avoided by providing a front edge 9 of the flexible sleeve 4 with a curved contour which is not possible for most instruments or fibers or might only be manufactured at increased costs.

FIG. 3 shows an instrument 1 which is completely introduced into the working channel 2 wherein the proximal end region 3 protrudes from the proximal end region 10 of the working channel 2. The proximal end region 3 contacts a renal calculus 11. In case of instrument 1 being a fiber for light emitted by a laser, the renal calculus 11 might be fragmented by a pulse of the laser which is transferred and delivered by the fiber. The protective cover 4 is pulled back relative to the instrument 1. Such pulling back might be done by the physician by manually pulling the proximal end region 6. However, it is also possible to use an automated device for such causing such movement. The protective sleeve 4 is pulled back relative to the instrument 1 as far as necessary for freeing the distal end 3 such that the distal end 3 is located outside the flexible sleeve 4. The distance the flexible sleeve 4 is pulled back might depend on the design and function of instrument 1. Asides from the configuration shown in FIG. 3, it might be possible that the two distal end regions 3 and 5 are located in a common plane. It is also possible that the distal end region 3 of instrument 1 is located slightly inside the flexible sleeve 4 adjacent to the distal tip of the flexible sleeve 4. The step of pulling back the flexible sleeve 4 is performed after having completely inserted instrument 1 into working channel 2. In such state instrument 1 extends from the proximal end region to the distal end region of the flexible sleeve 4. The extension of the flexible sleeve 4 in axial direction is longer than that of the working channel 2. Such relation of the lengths guarantees that the proximal end region 6 of flexible sleeve 4 protrudes from the proximal end region of the working channel 2 after completion of the insertion of instrument 1.

FIG. 4 shows a similar arrangement than that of FIG. 3. However, according to FIG. 4, flexible sleeve 4 is completely removed and pulled back from the working channel so that only instrument 1 is located inside the working channel. For such embodiment the length of instrument 1 doubles or is larger than the double of the length of the flexible sleeve 4. The flexible sleeve 4 might have a length of approximately 70 cm. One typical fiber building an instrument 1 might have a length of approximately 3 m.

According to one embodiment of the invention, the working channel 2 is a working channel of a flexible ureterorenoscope of the company KARL STORZ sold under the trademark Flex-X. The working channel 2 of the endoscope preferably comprises an inner diameter of approximately 1.1 mm. In such case the instrument 1 might be embodied in a glass fiber for transmitting energy emitted by a laser. Such glass fiber is sold by the applicant under the trademark FlexiFib and comprises an outer diameter of 0.43 mm. The flexible sleeve might be made of PTFE and might have an inner diameter of approximately 0.7 mm and an outer diameter of approximately 0.9 mm. Accordingly, the flexible sleeve 4 might comprises a wall thickness of 0.1 mm. The proximal end region of the flexible sleeve is linked with a Touhy Borst adapter which is sized such that it might be reversibly crimped against the outer diameter of the glass fiber without damaging the glass fiber. The glass fiber is introduced into the flexible sleeve until the glass fiber protrudes approximately 3 to 5 mm from the distal end region 3. In such arrangement the Touhy Borst adapter is crimped with the glass fiber. With such fixation the flexible sleeve with the glass fiber embedded therein might be introduced into the working channel 2 of the ureterorenoscope without damaging the limiting wall of working channel 2 by the glass fiber also in cases where the ureterorenoscope is extremely curved. When the distal end region 3 of the glass fiber has passed through the distal end region 10 of the working channel 2, the Touhy Borst adapter is released and the flexible sleeve 4 is removed and pulled out of the working channel 2. The position of the glass fiber relative to the endoscope is fixed when removing the flexible sleeve 4. According to another embodiment of the invention, the flexible sleeve might have a length of approximately 1 m.

The outer diameter of the flexible sleeve might be 0.9 mm which is appropriate for 3.6 Fr working channels. The clearance might be 0.6 mm for commonly used laser fibers.

FIG. 5 shows a curved region of a working channel 2 with a flexible sleeve 4 with an embedded instrument 1 located therein. According to the embodiment shown in FIG. 5, the distal end 5 is slanted or cut with an angle which differs from a direction perpendicular to the longitudinal axis of the flexible sleeve 4. The distal end region 5 might be cut in a straight or curved plane. The end region 5 might have a front face 12 with an elliptical outer and inner geometry.

Figure 6:
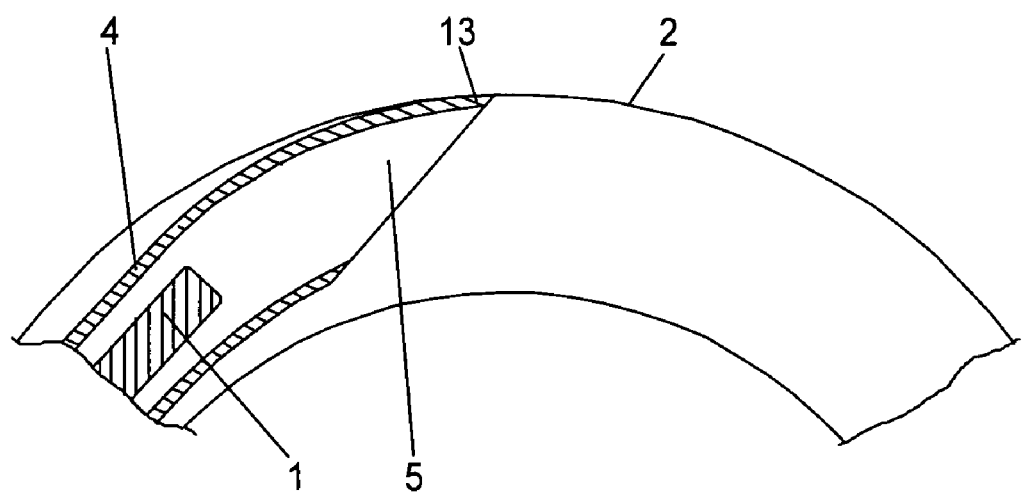
FIG. 6 shows a slanted distal end region of a flexible sleeve with a fiber located therein during advancement of the flexible sleeve and the fiber through a region of the working channel with changed rotational angle of the flexible sleeve.

The sloped design of the distal end region 3 has two effects shown in FIG. 5 and FIG. 6:

According to FIG. 5, the sloped end region 3 might result in a front face 12 which anticipates the curvature of the working channel 2 such that the front face contacts the working channel at a small angle and maybe with an increased contact surface.

According to FIG. 6, for a different orientation of the flexible sleeve it might be helpful that due to the sloped distal end region 5 of the flexible sleeve 4 the cross section of the distal end region decreases continuously to 0 in the direction of the distal tip 13 of the flexible sleeve 4. This means that the distal tip of the end region might be easily deflected such that the distal end region 5 easily assimilates to the curvature of the working channel 2. The elasticity of the flexible sleeve 4 might additionally be reduced by providing at least the distal end region 5 with bores, slots and the like. The distal end region 3 of the instrument 1 is preferably located with a small distance from the slanted end region 5 where the full cross section is available in order to provide fill coverage of any edges of the end region 3.

FIGS. 1, 2, 5 and 6 show the endoscope in a first operational state whereas FIG. 4 shows the endoscope in a second operational state and FIG. 3 shows the endoscope in a third operational state.

Many variations and modifications may be made to the preferred embodiments of the invention without departing substantially from the spirit and principles of the invention. All such modifications and variations are intended to be included herein within the scope of the present invention, as defined by the following claims.

I claim:

1. A method for using an endoscope including a working channel having a proximal end, a distal end, and an inner surface, an optical fiber having a proximal end, a distal end, and an outer surface, and a flexible sleeve in a body, said method comprising the steps of:
   a) embedding the optical fiber in the flexible sleeve in a first operational state and locating the distal end of the optical fiber inside the flexible sleeve, the flexible sleeve covering the distal end of the optical fiber, the distal end of the optical fiber positioned proximally of a distal tip of the flexible sleeve;
   b) introducing the flexible sleeve with the optical fiber embedded therein into a working channel of the endoscope and extending the distal tip of the flexible sleeve from the distal end of the working channel;
   c) retracting the flexible sleeve relative to the optical fiber and relative to the working channel so that the distal end of the optical fiber extends from the distal tip of the flexible sleeve and from the distal end of the working channel to form a lumen between the inner surface of the working channel and the outer surface of at least one of the optical fiber and the flexible sleeve, wherein the step of retracting the flexible sleeve further comprises retracting the flexible sleeve substantially completely from the working channel in a second operational state so that only the optical fiber is located within the working channel, and the method further comprises the step of reintroducing the flexible sleeve into the working channel prior to removing the flexible sleeve with the fiber located therein from the body;
   d) using the lumen for at least one purpose selected from the group consisting of a diagnostic purpose, a therapeutic purpose, delivery of fluid, and collection of fluid, and
   e) removing the flexible sleeve with the fiber located therein from the body.

2. A method for use of an endoscope according to claim 1, wherein said step of using the lumen for at least one of a group of a diagnostic and a therapeutic purpose comprises introducing an instrument into said lumen.

3. A method for use of an endoscope according to claim 1, wherein said step of using the lumen for at least one of a group of a diagnostic and a therapeutic purpose comprises using the lumen for delivery or collection of a fluid.

4. A method for use of an endoscope according to claim 1, further comprising the steps of
   introducing the endoscope into a human body before performing said said steps of embedding and introducing and
   removing the endoscope from said human body after performing said step of removing.

5. The method of claim 1, wherein the flexible sleeve is a polytetrafluoroethylene sleeve.

6. The method of claim 1, further comprising the step of linking a proximal end of the flexible sleeve with the optical fiber embedded therein with a Touhy Borst adapter.

* * * * *